United States Patent
Brown et al.

(10) Patent No.: US 10,695,289 B2
(45) Date of Patent: Jun. 30, 2020

(54) ZINC COMPOSITIONS FOR COATED MICRONEEDLE ARRAYS

(71) Applicant: 3M INNOVATIVE PROPERTIES COMPANY, St. Paul, MN (US)

(72) Inventors: Kenneth E. Brown, Inver Grove Heights, MN (US); Daniel M. Dohmeier, White Bear Lake, MN (US); Joan T. Moseman, Lake Elmo, MN (US); Ying Zhang, Woodbury, MN (US); Alan Harris, New York City, NY (US); Gary Hattersley, Stow, MA (US); Lisa A. Dick, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 58 days.

(21) Appl. No.: 15/766,469

(22) PCT Filed: Oct. 7, 2016

(86) PCT No.: PCT/US2016/055924
§ 371 (c)(1),
(2) Date: Apr. 6, 2018

(87) PCT Pub. No.: WO2017/062727
PCT Pub. Date: Apr. 13, 2017

(65) Prior Publication Data
US 2018/0289615 A1 Oct. 11, 2018

Related U.S. Application Data

(60) Provisional application No. 62/239,773, filed on Oct. 9, 2015, provisional application No. 62/239,774, filed on Oct. 9, 2015, provisional application No. 62/239,801, filed on Oct. 9, 2015, provisional application No. 62/268,757, filed on Dec. 17, 2015, provisional application No. 62/324,336, filed on Apr. 18, 2016, provisional application No. 62/353,249, filed on Jun. 22, 2016, provisional application No. 62/396,196, filed on Sep. 18, 2016.

(51) Int. Cl.
*A61K 9/00* (2006.01)
*A61K 47/02* (2006.01)
*A61K 38/00* (2006.01)
*A61B 17/20* (2006.01)
*A61B 17/00* (2006.01)

(52) U.S. Cl.
CPC .......... *A61K 9/0021* (2013.01); *A61K 9/0014* (2013.01); *A61K 47/02* (2013.01); *A61B 17/205* (2013.01); *A61B 2017/00526* (2013.01); *A61K 38/00* (2013.01)

(58) Field of Classification Search
None
See application file for complete search history.

(56) References Cited

U.S. PATENT DOCUMENTS

| | | |
|---|---|---|
| 6,881,203 B2 | 4/2005 | Delmore et al. |
| 8,741,377 B2 | 6/2014 | Choi et al. |
| 9,339,956 B2 | 5/2016 | Bendon |
| 2004/0049150 A1 | 3/2004 | Dalton et al. |
| 2004/0265354 A1 | 12/2004 | Amen et al. |
| 2005/0032698 A1 | 2/2005 | Day |
| 2005/0261631 A1 | 11/2005 | Clarke et al. |
| 2006/0195067 A1 | 8/2006 | Wolter et al. |
| 2009/0016935 A1 | 1/2009 | Andrianov et al. |
| 2011/0281790 A1 | 11/2011 | Pohl |
| 2013/0006217 A1 | 1/2013 | Hattersley |
| 2013/0041330 A1 | 2/2013 | Matsudo |
| 2014/0046293 A1 | 2/2014 | Hattersley et al. |

FOREIGN PATENT DOCUMENTS

| WO | WO 2010/059605 | 5/2010 |
|---|---|---|
| WO | WO 2010/117602 | 10/2010 |

OTHER PUBLICATIONS

A Transdermal Patch Delivering the PTHrP1-34 Analog, Abaloparatide (BA058) Dose-Dependent Increases Spine and Hip BMD Compared to Placebo, Osteoporosis Clinical Trials, Endocrine Society. (Year: 2014).
Gary Hattersley et al: "Transdermal delivery of BA058, a novel analog of hPTHrP (1-34), with a short wear time patch in preclinical and clinical studies", Bone Abstracts, May 1, 2013 (May 1, 2013).
Shirkhanzadeh M: "Microneedles coated with porous calcium phosphate ceramics: Effective vehicles for transdermal delivery of solid trehalose", Journal of Materials Science: Materials in Medicine, val. 16, No. 1, Jan. 1, 2005 (Jan. 1, 2005 ), pp. 37-45.

*Primary Examiner* — David J Blanchard
*Assistant Examiner* — Daniel F. Coughlin
(74) *Attorney, Agent, or Firm* — Mueting Raasch Group

(57) ABSTRACT

A medical device comprising a composition comprising a therapeutically active amount of active agent, a zinc compound, and an array of microneedles. The zinc compound may be selected from the group consisting of zinc, pharmaceutically acceptable salts of zinc, and mixtures thereof. At least a portion of the composition is present as a coating on at least a portion of the microneedles. Methods of delivering a therapeutically active agent to a mammal using compositions of the disclosure are also included.

19 Claims, 2 Drawing Sheets

ZINC COMPOSITIONS FOR COATED MICRONEEDLE ARRAYS

CROSS REFERENCE TO RELATED APPLICATIONS

This application is a national stage filing under 35 U.S.C. 371 of PCT/US2016/055924, filed Oct. 7, 2016, which claims the benefit of U.S. Provisional Patent Application Nos. 62/239,773, 62/239,774 and 62/239,801, filed Oct. 9, 2015; 62/268,757, filed Dec. 17, 2015; 62/324,336, filed Apr. 18, 2016; 62/353,249, filed Jun. 22, 2016 and 62/396,196, filed Sep. 18, 2016, the disclosures of which are incorporated by reference in their entirety herein.

FIELD

The present disclosure relates to microneedle arrays with useful compositions. The present disclosure also relates to methods of delivering therapeutically active agents to a mammal with a coated microneedle array.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Microneedle devices having a fluid reservoir and conduits through which a therapeutic substance may be delivered to the skin have been proposed, but there remain a number of difficulties with such systems, such as the ability to make very fine channels that can reliably be used for fluid flow.

Microneedle devices having a dried coating on the surface of a microneedle array have desirable features compared to fluid reservoir devices. The devices are generally simpler and can directly introduce a therapeutic substance into the skin without the need for providing reliable control of fluid flow through very fine channels in the microneedle device.

Coated microneedle devices typically deliver therapeutic substances into the intradermal space and it is known that at least in some instances the pharmacokinetic profile obtained with intradermal delivery may differ from that of other delivery routes, such as subcutaneous and intravenous.

BRIEF SUMMARY

In one embodiment, the disclosure is a medical device comprising a composition comprising a therapeutically active amount of an active agent, a zinc compound selected from the group consisting of zinc, pharmaceutically acceptable salts of zinc, and mixtures thereof, and an array of microneedles. At least a portion of the composition is present as coating on at least a portion of the microneedles.

In one embodiment, the disclosure is a method of delivering a therapeutically active agent to a mammal, comprising applying a device of the present disclosure to a skin surface of the mammal, allowing the device to remain in contact with the skin for a period of time to allow a portion of the active agent to be transferred into the skin of the mammal, and subsequently removing the device from the mammal.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
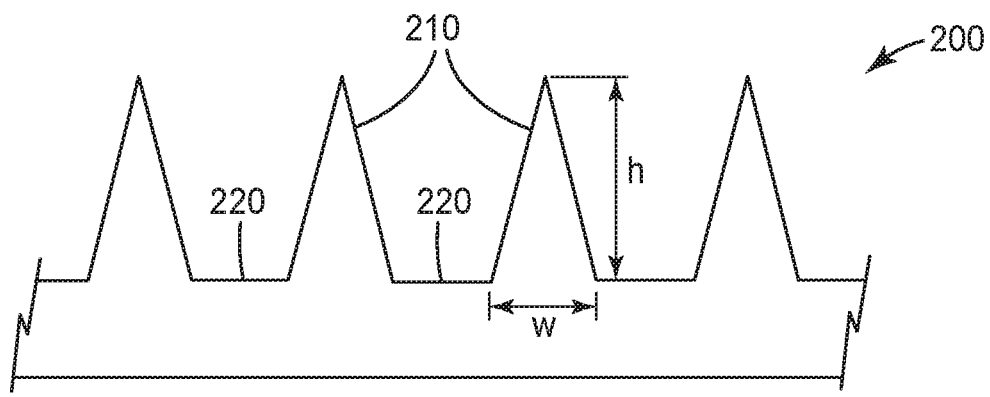
FIG. 1 is a schematic cross-sectional view of an uncoated microneedle array.

In the following description, reference is made to the accompanying drawing that forms a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Compositions disclosed herein include at least one active pharmaceutical ingredient (referred to herein as an "API" or active agent); and an excipient comprising a zinc compound. In one embodiment, the zinc compound may be selected from the group consisting of zinc, pharmaceutically acceptable salts of zinc, and mixtures thereof.

In one embodiment the zinc compound comprises an inorganic salt of zinc. Suitable inorganic salts of zinc may include, for example, zinc chloride. In one embodiment the zinc compound comprises zinc chloride.

In one embodiment the zinc compound consists essentially of zinc chloride. By consists essentially of zinc chloride, it is meant that the zinc compound of the disclosure may contain minimal amounts of zinc or other salts of zinc to the extent that these minimal amounts have no detectable effect on the functional properties of the composition, such as the effect on pharmacokinetic parameters such as Cmax and AUC, as described in more detail below. It should be understood that if only minimal amounts of compounds other than zinc chloride are present, such as if 99% or more by weight of the total zinc compound is zinc chloride, then the zinc compound consists essentially of zinc chloride. In one embodiment, the zinc compound consists of zinc chloride.

In one embodiment 90% or more by weight of the zinc compound is present as zinc chloride. In one embodiment 95% or more by weight of the zinc compound is present as zinc chloride. In one embodiment 98% or more by weight of the zinc compound is present as zinc chloride. In one embodiment 99% or more by weight of the zinc compound is present as zinc chloride.

In one embodiment the zinc compound comprises an organic salt of zinc. Suitable organic salts of zinc may include, for example, zinc acetate. In one embodiment the zinc compound comprises zinc acetate.

In one embodiment the zinc compound consists essentially of zinc acetate. By consists essentially of zinc acetate, it is meant that the zinc compound of the disclosure may contain minimal amounts of zinc or other salts of zinc to the extent that these minimal amounts have no detectable effect on the functional properties of the composition, such as the effect on pharmacokinetic parameters such as Cmax and AUC, as described in more detail below. It should be understood that if only minimal amounts of compounds other than zinc acetate are present, such as if 99% or more by weight of the total zinc compound is zinc acetate, then the zinc compound consists essentially of zinc acetate. In one embodiment, the zinc compound consists of zinc acetate.

In one embodiment 90% or more by weight of the zinc compound is present as zinc acetate. In one embodiment 95% or more by weight of the zinc compound is present as zinc acetate. In one embodiment 98% or more by weight of the zinc compound is present as zinc acetate. In one embodiment 99% or more by weight of the zinc compound is present as zinc acetate.

In one embodiment, the zinc compound comprises a divalent salt of zinc. Suitable divalent salts of zinc include zinc chloride and zinc acetate.

In one embodiment the zinc compound consists essentially of divalent salt of zinc. By consists essentially of divalent salt of zinc, it is meant that the zinc compound of the disclosure may contain minimal amounts of metallic zinc (i.e., Zn(0)) or non-divalent salts of zinc to the extent that these minimal amounts have no detectable effect on the functional properties of the composition, such as the effect on pharmacokinetic parameters such as Cmax and AUC, as described in more detail below. It should be understood that if only minimal amounts of compounds other than divalent salts of zinc are present, such as if 99% or more by weight of the total zinc compound is a divalent salt of zinc, then the zinc compound consists essentially of a divalent salt of zinc. In one embodiment, the zinc compound consists of a divalent salt of zinc.

In one embodiment 90% or more by weight of the zinc compound is present as a divalent salt of zinc. In one embodiment 95% or more by weight of the zinc compound is present as a divalent salt of zinc. In one embodiment 98% or more by weight of the zinc compound is present as a divalent salt of zinc. In one embodiment 99% or more by weight of the zinc compound is present as a divalent salt of zinc.

In embodiments, the molar ratio of zinc compound to API is greater than 0.1, greater than 0.2, or greater than 0.25. In embodiments, the molar ratio of zinc compound to API is less than 2.0, less than 1.5, or less than 1.0. In one embodiment, the molar ratio of zinc compound to API is between 0.1 and 2.0. In one embodiment, the molar ratio of zinc compound to API is between 0.2 and 1.5. In one embodiment, the molar ratio of zinc compound to API is between 0.25 and 1.0. In one embodiment, the molar ratio of zinc compound to API is about 0.5. In one embodiment, the molar ratio of zinc compound to API is about 0.75. In one embodiment, the molar ratio of zinc compound to API is about 1.0.

In embodiments, the amount of zinc compound is greater than 0.5%, greater than 1%, or greater than 2% of the total weight of the composition. In embodiments, the amount of zinc compound is less than 10%, less than 8%, or less than 6% of the total weight of the composition. In one embodiment, the amount of zinc compound is between 0.5 and 10% of the total weight of the composition. In one embodiment, the amount of zinc compound is between 1 and 8% of the total weight of the composition. In one embodiment, the amount of zinc compound is between 2 and 6% of the total weight of the composition. In one embodiment, the amount of zinc compound is about 3% of the total weight of the composition. In one embodiment, the amount of zinc compound is about 4% of the total weight of the composition. In one embodiment, the amount of zinc compound is about 5% of the total weight of the composition.

The at least one API can generally include any pharmacologically active component. The at least one API can include vaccines, hormones, proteins, peptides, lipoproteins, glycoproteins, polysaccharides, lipopolysaccharides, oligosaccharides, glycolipids, polynucleotide sequences, DNA vaccines, and antibiotics such as ceftriaxone. In one embodiment, the API is selected from the group consisting of hormones, proteins, peptides, lipoproteins, glycoproteins, polysaccharides, lipopolysaccharides, oligosaccharides, glycolipids, polynucleotide sequences, and antibiotics. In one embodiment, the API is a protein or a peptide.

The at least one API can also be a small molecule that may be otherwise difficult or impossible to deliver by passive transdermal delivery. Examples of such molecules include ionic molecules, such as bisphosphonates, for example sodium alendronate or pamedronate; molecules with physicochemical properties that are not conducive to passive transdermal delivery such as naltrexone, and lidocaine for example.

The at least one API can also include agents for dermatological treatments, vaccine delivery, or enhancement of an immune response with vaccine adjuvants. Examples of suitable vaccines include DNA vaccine, cellular vaccines such as a dendritic cell vaccine, recombinant protein vaccine, therapeutic cancer vaccine, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, polio vaccine, herpes vaccine, human papilloma virus vaccine, rotavirus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes antigens in the forms of proteins, peptides, lipoproteins, glycoproteins, polysaccharides, lipopolysaccharides, oligosaccharides, glycolipids, polynucleotide sequences, weakened or killed viruses, virus particles, virus-like particles, weakened or killed bacteria, bacterial cell walls, toxoids, and desensitizing agents such as cat, dust, or pollen allergens. Additional examples of suitable vaccines and vaccine adjuvants are described in United States Patent Application Publication Nos. 2004/0049150, 2004/0265354, and US2006/0195067, the disclosures of which are incorporated herein by reference.

In embodiments that include an API that is a vaccine, the aqueous formulation can also optionally include one or more adjuvants. An adjuvant is an agent that modifies the effect of another agent (in this case the vaccine API). Adjuvants are often utilized to enhance the recipient's immune response to the vaccine. The particular identity of the adjuvant can depend at least in part on the identity of the API vaccine. Adjuvants can include aluminum phosphate, aluminum phosphate gel, aluminum hydroxide, squalene, beta-glucan, CpG containing oligonucleotides, QS-21, glucosaminylmuramyl dipeptide (GMDP), murametide, dimethyldioctadecylammonium bromide (DDA), Quil A, threonyl-muramyl dipeptide (threonyl-MDP), MTP-PE, MTP-PE liposomes, a 4-amino-imidazo[4,5-c]quinoline based immune response modifier compound, a 4-amino[1,3]thiazolo[4,5-c]quinoline based immune response modifier compound, a TLR6 agonist, a TLR7 agonist, a TLR8 agonist, a TLR9 agonist, imiquimod, resiquimod, 2-propyl[1,3]thiazolo[4,5-c]quinolin-4-amine, IL-2, IL-4, IL-10, IL-12, IL-15, IL-18, and combinations thereof.

In embodiments, the at least one API can be a composition of matter or mixture containing a component that is pharmacologically effective when administered in an amount of less than about 5 mg, and in some embodiments less than about 0.25 mg.

In embodiments the API includes, for example, human growth hormone (hGH), tissue plasminogen activator (TPA), calcitonin gene related peptide (CGRP), leutinizing hormone releasing hormone (LHRH), LHRH analogs (such as goserelin, leuprolide, buserelin, triptorelin), gonadorelin, and napfarelin, menotropins (follicle stimulating hormone (FSH) and leutinizing hormone (LH)), human menopausal goanadotropins (hMG), human chorionic gonadotropin (hCG), vasopressin, desmopressin, insulin, adrenocortiocotropic hormone (ACTH), ACTH analogs such as ACTH (1-24), calcitonin, parathyroid hormone (PTH), parathyroid hormone antagonists, parathyroid horomone-related protein (PTHrP), parathyroid hormone-related protein analogues, which can be, without limitation, one or more of, oxytocin, deamino [Val4, D-Arg8] arginine vasopressin, interferon alpha, interferon beta, interferon gamma, tumor necrosis factor (TNF), erythropoietin (EPO), granulocyte macrophage colony stimulating factor (GM-CSF), granulocyte colony stimulating factor (G-CSF), interleukins, interleukin-2 (IL-2), interleukin-10 (IL-10), glucagon, and growth hormone releasing factor (GRF). The agents can be in various forms, such as free bases, acids, charged or uncharged molecules, components of molecular complexes or nonirritating, pharmacologically acceptable salts. Also, simple derivatives of the agents (such as ethers, esters, amides, etc) which are physiologically hydrolyzed at body pH, enzymes, etc., can be employed.

In some embodiments the API is human growth hormone (hGH).

In some embodiments the API is tissue plasminogen activator (TPA).

In some embodiments the API is calcitonin gene related peptide (CGRP).

In some embodiments the API is leutinizing hormone releasing hormone (LHRH).

In some embodiments the API is goserelin.

In some embodiments the API is leuprolide.

In some embodiments the API is buserelin.

In some embodiments the API is triptorelin.

In some embodiments the API is gonadorelin.

In some embodiments the API is napfarelin.

In some embodiments the API is follicle stimulating hormone (FSH).

In some embodiments the API is leutinizing hormone (LH).

In some embodiments the API is human menopausal goanadotropins (hMG).

In some embodiments the API is human chorionic gonadotropin (hCG).

In some embodiments the API is vasopressin.

In some embodiments the API is desmopressin.

In some embodiments the API is insulin.

In some embodiments the API is adrenocortiocotropic hormone (ACTH),

In some embodiments the API is an ACTH analogs, such as ACTH (1-24).

In some embodiments the API is calcitonin.

In some embodiments the API is parathyroid hormone (PTH).

In some embodiments the API is a parathyroid hormone antagonist.

In some embodiments the API is parathyroid hormone-related protein (PTHrP).

In some embodiments the API is oxytocin.

In some embodiments the API is deamino [Val4, D-Arg8] arginine vasopressin.

In some embodiments the API is interferon alpha.

In some embodiments the API is interferon beta.

In some embodiments the API is interferon gamma.

In some embodiments the API is tumor necrosis factor (TNF).

In some embodiments the API is erythropoietin (EPO).

In some embodiments the API is granulocyte macrophage colony stimulating factor (GM-CSF).

In some embodiments the API is granulocyte colony stimulating factor (G-CSF).

In some embodiments the API is an interleukin.

In some embodiments the API is glucagon.

In some embodiments the API is growth hormone releasing factor (GRF).

In embodiments the API includes, for example, human growth hormone (hGH), tissue plasminogen activator (TPA), calcitonin gene related peptide (CGRP), leutinizing hormone releasing hormone (LHRH), LHRH analogs (such as goserelin, leuprolide, buserelin, triptorelin), gonadorelin, and napfarelin, menotropins (follicle stimulating hormone (FSH) and leutinizing hormone (LH)), human menopausal goanadotropins (hMG), human chorionic gonadotropin (hCG), vasopressin, desmopressin, insulin, adrenocortiocotropic hormone (ACTH), ACTH analogs such as ACTH (1-24), calcitonin, parathyroid hormone (PTH), parathyroid hormone antagonists, parathyroid horomone-related protein (PTHrP), oxytocin, deamino [Val4, D-Arg8] arginine vasopressin, interferon alpha, interferon beta, interferon gamma, tumor necrosis factor (TNF), erythropoietin (EPO), granulocyte macrophage colony stimulating factor (GM-CSF), granulocyte colony stimulating factor (G-CSF), interleukins, interleukin-2 (IL-2), interleukin-10 (IL-10), glucagon, and growth hormone releasing factor (GRF). The agents can be in various forms, such as free bases, acids, charged or uncharged molecules, components of molecular complexes or nonirritating, pharmacologically acceptable salts. Also, simple derivatives of the agents (such as ethers, esters, amides, etc) which are physiologically hydrolyzed at body pH, enzymes, etc., can be employed.

In some embodiments, the active is not a parathyroid hormone-related protein analogue.

Compositions can also include additional components, such as a second (or subsequent) API, a second (or subsequent) excipient, components not noted herein, or some combination thereof.

Additional excipients can function, for example, to maintain the active nature of the API, to facilitate the coating performance of the formulation, or a combination thereof. The particular excipient to be utilized can depend at least in part on the particular API (or APIs) that are included in the composition.

Exemplary excipients can include for example buffers, carbohydrates, polymers, amino acids, polyamino acids, surfactants, proteins, non-aqueous solvents, inorganic salts, acids, bases, antioxidants and saccharin.

In embodiments, disclosed compositions can optionally include at least one buffer as an excipient. A buffer can generally function to stabilize the pH of an aqueous formulation that can be used to prepare the disclosed compositions. The particular buffer to be utilized can depend at least in part on the particular API (or APIs) that are included in the aqueous formulation. The pH of the aqueous formulation can be important, for example, to maintain the solubility of the API at a desired level. Generally, any commonly utilized buffers can be used in disclosed aqueous formulations and compositions.

Exemplary buffers can include for example, histidine, phosphate buffers, acetate buffers, citrate buffers, glycine buffers, ammonium acetate buffers, succinate buffers, pyrophosphate buffers, Tris acetate (TA) buffers, and Tris buffers. Buffered saline solutions can also be utilized as buffers. Exemplary buffered saline solutions include, for example, phosphate buffered saline (PBS), Tris buffered saline (TBS), saline-sodium acetate buffer (SSA), saline-sodium citrate buffer (SSC). In embodiments, PBS can be utilized as the buffer.

In embodiments, compositions can optionally include at least one carbohydrate, such as a sugar. Suitable sugars can include for example non-reducing sugars such as raffinose, stachyose, sucrose, and trehalose; and reducing sugars such as monosaccharides and disaccharides. Exemplary monosaccharides can include apiose, arabinose, digitoxose, fucose, fructose, galactose, glucose, gulose, hamamelose, idose, lyxose, mannose, ribose, tagatose, and xylose. Exemplary disaccharides can include for example cellobiose, gentiobiose, lactose, lactulose, maltose, melibiose, primeverose, rutinose, scillabiose, sophorose, turanose, and vicianose. In embodiments, sucrose, trehalose, fructose, maltose, or combinations thereof can be utilized. All optical isomers of exemplified sugars (D, L, and racemic mixtures) are also included herein.

In embodiments, compositions can optionally include at least one carbohydrate, such as a polysaccharide. Suitable polysaccharides can include for example starches such as hydroxyethyl starch, pregelantized corn starch, pentastarch, dextrin, dextran or dextran sulfate, gamma-cyclodextrin, alpha-cyclodextrin, beta-cyclodextrin, glucosyl-alpha-cyclodextrin, maltosyl-alpha-cyclodextrin, glucosyl-beta-cyclodextrin, maltosyl-beta-cyclodextrin, 2-hydroxy-beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-alpha-cyclodextrin, sulfobutylether-beta-cyclodextrin, and sulfobutylether-gamma-cyclodextrin. In embodiments, hydroxyethyl starch, dextrin, dextran, gamma-cyclodextrin, beta-cyclodextrin, or combinations thereof can be utilized. In embodiments, dextrans having an average molecular mass of 35,000 to 76,000 can be utilized.

In embodiments, compositions can optionally include at least one carbohydrate, such as a cellulose. Suitable celluloses can include for example hydroxyethyl cellulose (HEC), methyl cellulose (MC), microcrystalline cellulose, hydroxypropyl methyl cellulose (HPMC), hydroxyethylmethyl cellulose (HEMC), hydroxypropyl cellulose (HPC), and mixtures thereof.

In embodiments, compositions can optionally include at least one polymer, such as for example, polyvinyl pyrrolidone (PVP), polyethylene glycol (PEG), polyvinyl alcohol (PVA), and polyethylene glycol sorbitan isostearate. In embodiments, polyvinyl pyrrolidones (PVP) having an average molecular weight of 10,000 can be utilized. In embodiments, polyvinyl pyrrolidones (PVP having an average molecular weight of 5,000 to 1.5 million can be utilized. In embodiments, polyethylene glycols having an average molecular weight of 300 to 8,000 can be utilized.

In embodiments, compositions can optionally include at least one amino acid. Suitable amino acids can include for example lysine, histidine, cysteine, glutamate, lysine acetate, sarcosine, proline, threonine, asparagine, aspartic acid, glutamic acid, glutamine, isoleucine, leucine, methionine, phenylalanine, serubem tryptophan, tyrosine, valine, alanine, arginine, and glycine. In many cases the salt form of the amino acids can be used to increase the aqueous solubility of the amino acid in the compositions. In a preferred embodiment the compositions include histidine.

In embodiments, compositions can optionally include at least one polyamino acid. Suitable polyamino acids can include for example polyhistidine, polyaspartic acid, and polylysine. In embodiments, compositions can include at least one protein. Suitable proteins can include for example human serum albumin and bioengineered human albumin.

In embodiments, compositions can optionally include at least one surfactant which can be amphoteric, cationic, anionic, or nonanionic. Suitable surfactants can include for example lecithin, polysorbates (such as polysorbate 20, polysorbate 40, and polysorbate 80 for example), glycerol, sodium lauroamphoacetate, sodium dodecyl sulfate, cetylpyridinium chloride (CPC), dodecyltrimethyl ammonium chloride (DoTAC), sodium desoxycholate, benzalkonium chloride, sorbitan laurate, and alkoxylated alcohols (such as laureth-4).

In embodiments, compositions can optionally include at least one non-zinc containing inorganic salt. Suitable inorganic salts can include for example sodium chloride, and potassium chloride.

In embodiments, compositions can optionally include saccharin, for example saccharin sodium dihydrate. In embodiments, compositions can optionally include a lipid such as dipalmitoylphosphatidylcholine (DPPC) for example.

In embodiments, compositions can optionally include at least one weak acid, weak base, strong acid, strong base, or some combination thereof. Acids and bases can serve the purpose of solubilizing or stabilizing the API. These acids and bases can be referred to as counterions. These acids and bases can be organic or inorganic. Exemplary weak acids include for example acetic acid, propionic acid, pentanoic acid, citric acid, succinic acid, glycolic acid, gluconic acid, glucuronic acid, lactic acid, malic acid, pyruvic acid, tartaric acid, tartronic acid, fumaric acid, glutamic acid, aspartic acid, malonic acid, butyric acid, crotonic acid, digylcolide acid, and glutaric acid. Exemplary strong acids include for example hydrochloric acid, hydrobromic acid, nitric acid, sulfonic acid, sulfuric acid, maleic acid, phosphoric acid, benzene sulfonic acid, and methane sulfonic acid. Exemplary weak bases include for example ammonia, morpholine, histidine, lysine, arginine, monoethanolamine, diethanolamine, triethanolamine, tromethamine, methylglucamine, and glucosamine. Exemplary strong bases include for example sodium hydroxide, potassium hydroxide, calcium hydroxide, and magnesium hydroxide.

In embodiments, compositions can optionally include at least one antioxidant. Suitable antioxidants can include for example sodium citrate, citric acid, EDTA, ascorbic acid, methionine, sodium ascorbate, and combinations thereof.

The amounts of the various components in disclosed compositions can vary depending on the identity of the components in the components, the amount of API desired on the microneedle array, the amount of zinc compound present in the composition, the type of microneedle array being coated, other considerations not discussed herein, or some combination thereof.

Compositions can also be characterized based on the amount of API in the composition. In embodiments, a disclosed composition can have from 0.01% to 80% by weight of the at least one API; or from 0.1% to 70% by weight of the at least one API. In embodiments where an optional carbohydrate is employed, the compositions can also be characterized based on the amount of carbohydrate in the composition. In embodiments, a disclosed composition can have from 0% to 80% by weight of at least one carbohydrate; or from 5% to 70% by weight of at least one carbohydrate. In compositions where an optional polymer is employed, compositions can also be characterized based on the amount of polymer in the composition. In embodiments, a disclosed composition can have from 0% to 50% by weight of at least one polymer; or from 1% to 20% by weight of at least one polymer. In compositions where an optional surfactant is employed, compositions can also be characterized based on the amount of surfactant in the composition. In embodiments, a disclosed composition can have from 0% to 10% by weight of at least one surfactant; or from 0% to 5% by weight of at least one surfactant.

Compositions disclosed herein are typically prepared by coating a liquid formulation onto a microneedle array and then drying the liquid formulation so as to leave a dried composition on the microneedle array. The liquid formulations can also be referred to as coating formulations. Coating formulations disclosed herein can be further described by various properties of the formulations. Exemplary properties that can be utilized to further describe the coating formulations include for example, the viscosity of the coating formulation, the surface tension of the coating formulation, the contact angle of the coating formulation on the material of the microneedle, or some combination thereof.

Coating formulations disclosed herein often include water as a solvent and may also be referred to as aqueous formulations. Generally, the solvent composition in a coating formulation is selected such that it may dissolve or disperse the active pharmaceutical ingredient and excipients. Aqueous formulations disclosed herein can also include co-solvents in addition to water. In embodiments, an aqueous formulation can optionally include additional solvents (also referred to as co-solvents) such as ethanol, iospropanol, methanol, propanol, butanol, propylene glycol, dimethysulfoxide, glycerin, 1-methyl-2-pryrrolidinone, or N,N-dimethylformamide.

In embodiments, a coating formulation can be further characterized by its viscosity. Generally, viscosity is a measurement of the resistance of a fluid which is being deformed by either shear stress or tensile stress. In embodiments, disclosed coating formulations can be characterized by their resistance to being deformed by a shear stress, which can also be referred to as the shear viscosity of the aqueous formulation. Various instruments can be used for viscosity testing, including rheometers. In embodiments, the viscosity of a coating formulation can be measured using a rheometer, for example rheometers from TA Instruments (New Castle, Del.).

In embodiments, coating formulations disclosed herein can have a viscosity (or shear viscosity) of from 500 to 30,000 centipoise (cps) when measured at a shear rate of 100 $s^{-1}$ at a temperature of 25° C. In embodiments, coating formulations disclosed herein can have a viscosity (or shear viscosity) of from 500 to 10,000 cps when measured at a shear rate of 100 $s^{-1}$ at a temperature of 25° C. In embodiments, coating formulations disclosed herein can have a viscosity (or shear viscosity) of from 500 to 8,000 cps when measured at a shear rate of 100 $s^{-1}$ at a temperature of 25° C.

In embodiments, a coating formulation can be further characterized by its surface tension. Various methods can be utilized to measure surface tension. An exemplary type of surface tension measurement is based on the pendant drop method. In a pendant drop method of measuring surface tension, a drop of liquid is suspended from the end of a tube by surface tension. The force due to surface tension is proportional to the length of the boundary between the liquid and the tube. Various instruments that encompass optics systems for measuring the relevant parameters of the drop and software packages for calculating the surface tension based on the measured parameters can be utilized herein. An exemplary instrument includes the Drop Shape Analysis System (Model DSA 100S) available from Krüss (Hamburg, Germany).

In embodiments, coating formulations disclosed herein can have a surface tension (measured at ambient, or room temperature conditions) that is not greater than 60 dynes/cm. In embodiments, coating formulations disclosed herein can have a surface tension that is not greater than 55 dynes/cm. In embodiments, coating formulations disclosed herein can have a surface tension from 40 dynes/cm to 55 dynes/cm.

In embodiments, a coating formulation can be further characterized by its contact angle with the material of the microneedles (also referred to as the "microneedle material"). It should be noted that the contact angle of the coating formulation with respect to the microneedle material is measured on a horizontal substrate made of the microneedle material. The microneedle material can be (or include) silicon or a metal such as stainless steel, titanium, or nickel titanium alloy. The microneedle material can also be (or include) a medical grade polymeric material. Generally, the contact angle of a disclosed coating formulation with the microneedle material is an indication of the affinity of the coating formulation for the microneedle material. The lower the contact angle is, the stronger the attraction of the coating formulation for the microneedle material, resulting in increased wetting of the microneedle surface. The contact angle of the aqueous formulation on the microneedle material can be measured using various methods. In embodiments, the contact angle of the aqueous formulation on the microneedle material can be measured using the sessile drop method for example. Generally, a goniometer (or an instrument that employs a goniometer) can be utilized to measure contact angles, an example of such an instrument is the Drop Shape Analysis System (Model DSA 100S) available from Krüss (Hamburg, Germany). In embodiments, the contact angle can be measured within 5 seconds of the transfer of the coating formulation onto the substrate.

In embodiments, coating formulations disclosed herein can have a contact angle (measured at ambient, or room temperature conditions) with the microneedle material of 50° or greater. In embodiments, coating formulations disclosed herein can have a contact angle of 55° or greater. In embodiments, coating formulations disclosed herein can have a contact angle of 65° or greater. In embodiments, coating formulations disclosed herein can have a contact angle of 90° or less. In embodiments, coating formulations disclosed herein can have a contact angle of 80° or less.

In embodiments, the microneedle material can be a medical grade polymeric material. Exemplary types of medical grade polymeric materials include for example, polycarbonate and liquid crystalline polymer (referred to herein as "LCP").

Also disclosed herein are methods of delivering a therapeutically active agent to a mammal. Methods may include the step of applying a device to the skin of a mammal, wherein the device comprises an array of microneedles and the compositions disclosed herein and the composition is present as a coating on at least a portion of the microneedles. The device is allowed to remain in contact with the skin for a period of time to allow a portion of the active agent to be transferred into the skin of the mammal. The device is subsequently removed from the mammal.

Some examples of suitable mammals include humans, primates, pigs, cats, dogs, and rodents. In some embodiments the mammal is a human.

In some embodiments, the peak serum concentration of the active agent or $C_{max}$ attained in the mammal is greater than the $C_{max}$ that would be obtained if a like device with a composition lacking the zinc compound were applied to a mammal for a period of time. That is, inclusion of the zinc compound in the formulation causes an increase in $C_{max}$. In some embodiments, $C_{max}$ is about 1.2 times more than, about 1.5 times more than, or about 2 times more than a comparable device with a like composition lacking the zinc compound.

In some embodiments, the area-under-the-curve or AUC attained in the mammal is greater than the AUC that would be obtained if a like device with a composition lacking the zinc compound were applied to a mammal for a period of time. That is, inclusion of the zinc compound in the formulation causes an increase in AUC. In some embodiments, AUC is about 1.2 times more than, about 1.5 times more than, or about 2 times more than a comparable device with a like composition lacking the zinc compound.

In some embodiments, the bioavailability of the active agent attained in the mammal is greater than the bioavailability that would be obtained if a like device with a composition lacking the zinc compound were applied to a mammal for a period of time. That is, inclusion of the zinc compound in the formulation causes an increase in bioavailability. In some embodiments, the bioavailability is about 1.2 times more than, about 1.5 times more than, or about 2 times more than a comparable device with a like composition lacking the zinc compound.

In some embodiments, the time to achieve peak serum concentration of the active agent or $T_{max}$ attained in the mammal is greater than the $T_{max}$ that would be obtained if a like device with a composition lacking the zinc compound were applied to a mammal for a period of time. That is, inclusion of the zinc compound in the formulation causes an increase in $T_{max}$. In some embodiments, $T_{max}$ is about 1.2 times more than, about 1.5 times more than, or about 2 times more than a comparable device with a like composition lacking the zinc compound.

The period of time that the device is allowed to remain in contact with the skin may be chosen according to the active agent and type of composition used to achieve a desired therapeutic result. In some embodiments, the device is allowed to remain in contact with the skin for more than about 1 second, more than about 10 seconds, more than about 30 seconds, more than about 1 minute, or more than about 5 minutes. In some embodiments, the device is allowed to remain in contact with the skin for less than about 60 minutes, less than about 30 minutes, less than about 10 minutes, less than about 5 minutes, less than about 2 minutes, or less than about 1 minute. In some embodiments, the device is allowed to remain in contact with the skin for between about 10 seconds and 10 minutes, between about 30 seconds and 5 minutes, or between about 30 seconds and about 2 minutes.

Generally, an "array" refers to medical devices described herein that include more than one (in embodiments, a plurality) structure capable of piercing the stratum corneum to facilitate the transdermal delivery of therapeutic agents or the sampling of fluids through or to the skin. The terms "microstructure", or "microneedle" refer to the structures associated with an array that are capable of piercing the stratum corneum to facilitate the transdermal delivery of therapeutic agents or the sampling of fluids through or to the skin. By way of example, microstructures can include needle or needle-like structures as well as other structures capable of piercing the stratum corneum. The term "microneedle array" therefore can refer to a plurality of structures that are capable of piercing the stratum corneum to facilitate the transdermal delivery of therapeutic agents or the sampling of fluids through or to the skin.

Microneedle arrays useful in disclosed embodiments may include any of a variety of configurations, such as those described in the following patents and patent applications, the disclosures of which are incorporated herein by reference thereto. One embodiment for the microneedle arrays includes the structures disclosed in U. S. Patent Application Publication No. 2005/0261631 (the disclosure of which is incorporated herein by reference thereto), which describes microneedles having a truncated tapered shape and a controlled aspect ratio. A further embodiment for the microneedle arrays includes the structures disclosed in U.S. Pat. No. 6,881,203 (the disclosure of which is incorporated herein by reference thereto), which describes tapered microneedles with at least one channel formed on the outside surface. Another embodiment for the microneedle arrays includes the structures disclosed in PCT Publication No. WO2010/117602 (the disclosure of which is incorporated herein by reference thereto) and PCT Publication No. WO2010/059605 (the disclosure of which is incorporated herein by reference thereto), which both describe hollow microneedles.

Generally, a microneedle array can include a plurality of microneedles. FIG. 1 shows a portion of a microneedle array 200 that includes four microneedles 210 (of which two are referenced in FIG. 1) positioned on a microneedle substrate 220. Each microneedle 210 has a height h, which is the length from the tip of the microneedle 210 to the microneedle substrate 220. Either the height of a single microneedle or the average height of all microneedles on the microneedle array can be referred to as the height of the microneedle, h. In embodiments, each of the plurality of microneedles (or the average of all of the plurality of microneedles) can have a height of about 1 to 1200 micrometers (m). In embodiments, each of the plurality of microneedles can have a height of about 1 to 1000 μm. In embodiments, each of the plurality of microneedles can have a height of about 200 to 750 μm.

A single microneedle or the plurality of microneedles in a microneedle array can also be characterized by their aspect ratio. The aspect ratio of a microneedle is the ratio of the height of the microneedle, h, to the width (at the base of the microneedle), w (as seen in FIG. 1). The aspect ratio can be presented as h:w. In embodiments, each of the plurality of microneedles (or the average of all of the plurality of microneedles) can have an aspect ratio in the range of 2:1 to 5:1. In embodiments, each of the plurality of microneedles can have an aspect ratio of at least 2:1. In embodiments, each of the plurality of microneedles can have an aspect ratio of at least 3:1.

In embodiments, a microneedle or the plurality of microneedles in a microneedle array can also be characterized by their shape. In embodiments, each of the plurality of microneedles can have a square pyramidal shape or the shape of a hypodermic needle.

In embodiments a single microneedle or the plurality of microneedles in a microneedle array can also be characterized by its internal structure. In embodiments, each of the plurality of microneedles can have a cavity (for example a cylindrical cavity) extending the entire length of the microneedle (hollow microneedle), a cavity (for example a cylindrical cavity) extending through a portion of the microneedle (a partially hollow microneedle), or no internal cavity in the microneedle (solid microneedle). An internal cavity can provide a microneedle with additional surface area for coating the formulation and may allow for higher concentrations of API to be coated onto a microneedle.

Figure 2:
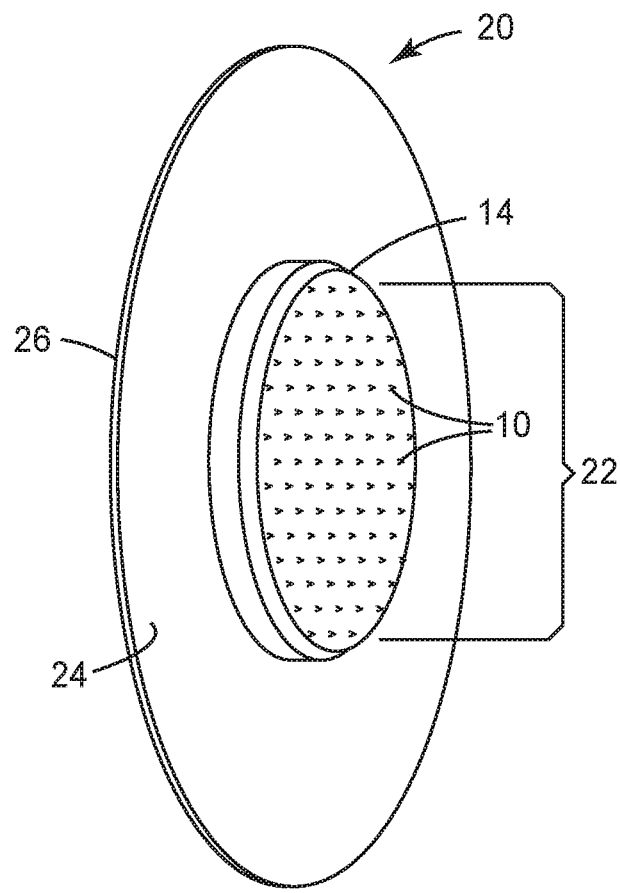
FIG. 2 is a schematic perspective view of a patch microneedle device.

In embodiments, a microneedle array may be applied to a skin surface in the form of a patch. Such an embodiment is shown in more detail in FIG. 2. FIG. 2 illustrates a device comprising a patch 20 in the form of a combination of a microneedle array 22, pressure sensitive adhesive 24 and backing 26. Such a patch 20, or a device including multiple microneedle arrays or multiple patches 20 can be referred to as a delivery device. A portion of the microneedle array 22 is illustrated with microneedles 10 protruding from a microneedle substrate 14. The microneedles 10 may be arranged in any desired pattern or distributed over the microneedle substrate 14 randomly. As shown, the microneedles 10 are arranged in uniformly spaced rows. In one embodiment, microneedle arrays can have a distal-facing surface area of more than about 0.1 cm$^2$ and less than about 20 cm$^2$; in embodiments more than about 0.5 cm$^2$ and less than about 5 cm$^2$. In one embodiment (not shown), a portion of the substrate 14 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 cm$^2$) to less than about 1 square inch (6.5 cm$^2$). In another embodiment (shown in FIG. 2), the microneedles are disposed over substantially the entire surface area of the array 22.

Once at least a portion of the solvent from the aqueous formulation has evaporated (either from a single contact step or multiple contact steps), the aqueous formulation on the microneedle array can be referred to as a coating composition. The coating composition can include at least the at least one API from the aqueous formulation. Alternatively, the coating composition can include a portion of the at least one excipient from the aqueous formulation, a portion of the solvent (water and optional co-solvents) from the aqueous formulation, or some combination thereof. The content of the coating composition on the coated microneedle array can depend at least in part on the aqueous formulation, the method of coating the microneedle array, the number of contacting steps, other optional steps, length and quantities of delays between contacting steps, the speed of withdrawal from the reservoir, other factors not discussed herein, or some combination thereof.

A microneedle array includes microneedles affixed to a substrate. In one embodiment, at least a portion of the composition is present on the microneedles. That is, at least a portion of the composition is not present on the substrate of the microneedle array. In one embodiment, at least 50% by weight of the composition is present on the microneedles. In one embodiment, at least 75% by weight of the composition is present on the microneedles. In one embodiment, at least 90% by weight of the composition is present on the microneedles.

EXAMPLES SECTION

Example 1—PTH/Zn

A coating formulation was prepared consisting of 7.45% rhPTH(1-34), (available from Bachem, Bubendorf, Switzerland), zinc chloride (0.19%), hydroxyethylcellulose 100 cP solution (2.07%), sucrose (39.88%), and water for injection (50.41%). Solid microneedle arrays made of liquid crystal polymer were prepared as described in U.S. Pat. No. 9,339,956. The arrays were 12.7 mm in diameter and had 316 square pyramidal needles with a height of 500 microns and tip to tip spacing of 550 microns. The arrays were dipped into the coating formulation to prepare tip-coated arrays as described in U.S. Pat. No. 8,741,377. The coated arrays were analyzed for rhPTH(1-34) content by HPLC and had an average content of 93 mcg (n=6). Solid microstructured transdermal (sMTS) patches were prepared by attaching the array to an adhesive overlay with a diameter of 27 mm.

Animal testing was performed with young, naïve, adult female mixed breed agricultural swine (Yorkshire X) with minimal skin pigmentation. The animals weighed approximately 22 to 30 kilograms at dosing. All animals were anesthetized prior to patch application. The test site (ham) was prepared by clipping, shaving, and scrubbing with a 3M Buf Puf and soapy water. Finally the test site was cleaned with a gauze pad soaked in 70% isopropyl alcohol solution and allowed to dry for at least 2 minutes prior to patch application. A single sMTS patch was applied to the test site at time 0. The patches remained on the skin for 15 minutes before removal. The skin surface was swabbed after patch removal and residual rhPTH left on the skin surface was determined by HPLC. Residual rhPTH on the post-application patch was also determined by HPLC. The difference between the initial content and the residual left on the skin and patch was used to determine a net delivered dose of 66 mcg.

Figure 3:
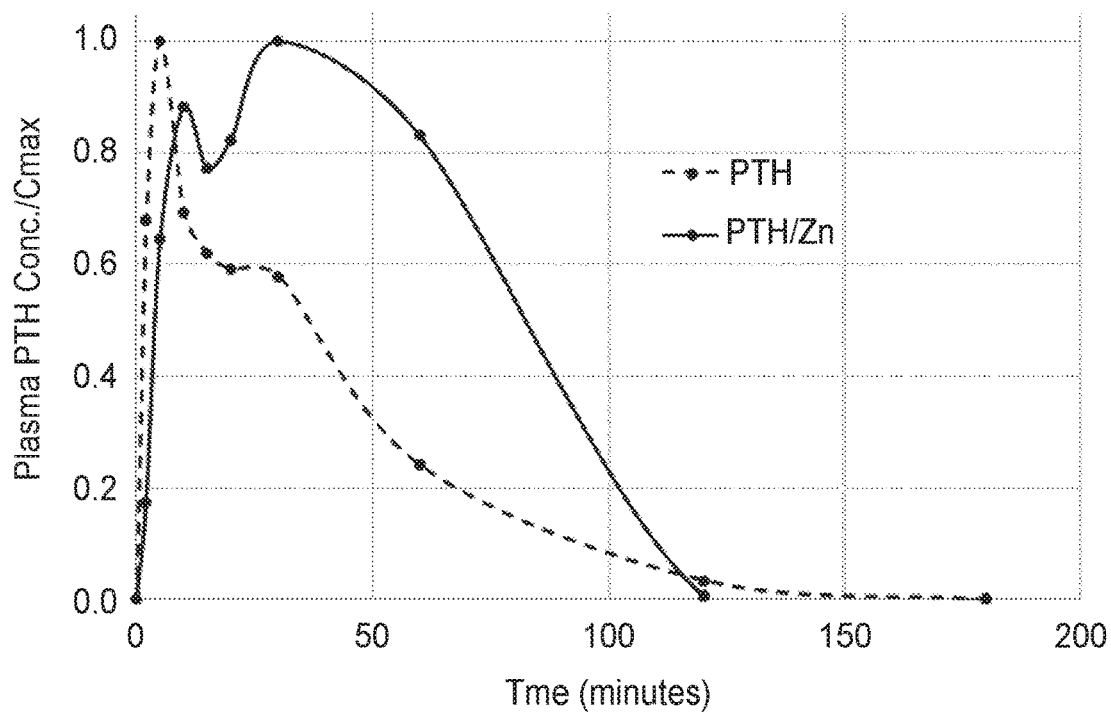
FIG. 3 is a graph of plasma PTH concentration/Cmax vs. time.

Blood draws (1.5 mL per time point) were taken from an ear vein at times 0 min (pre-application), 2 min, 5 min, 10 min, 15 min, 20 min, 30 min, 60 min, 120 min, and 180 min. Plasma sample volume was approximately 0.7 mL. Plasma was stored at −70° C. prior to analysis. Plasma samples were assayed using ELISA assay kits. rhPTH (1-34) standards were run on each individual plate to determine a standard curve for that plate. The average plasma levels (n=4) normalized by Cmax are shown in FIG. 3 as a solid line.

Comparative Example 1—PTH

A coating formulation was prepared consisting of 7.22% rhPTH(1-34), (available from Bachem, Bubendorf, Switzerland), hydroxyethylcellulose 100 cP solution (2.00%), sucrose (40.71%), and water for injection (50.06%). sMTS patches were prepared as described in Example 1. The coated arrays were analyzed for rhPTH(1-34) content by HPLC and had an average content of 66 mcg (n=6). The net delivered dose was 56 mcg. Animal testing and analysis was performed as described in Example 1 The average plasma levels (n=3) normalized by Cmax are shown in FIG. 3 as a dashed line.

Example 2—rhGH/Zn

A coating formulation was prepared consisting of 1.3% rhGH, (available from ProSpec-Tany TechnoGene Ltd., Ness Ziona, Israel), zinc chloride (0.014%), hydroxyethylcellulose 100 cP solution (2.4%), sucrose (39.85%), and water for injection (56.4%). Solid microneedle arrays made of liquid crystal polymer were prepared as described in U.S. Pat. No. 9,339,956. The arrays were 12.7 mm in diameter and had 316 square pyramidal needles with a height of 500 microns and tip to tip spacing of 550 microns. The arrays were dipped into the coating formulation to prepare tip-coated arrays as described in U.S. Pat. No. 8,741,377. The coated arrays were analyzed for rhGH content by HPLC and had an average content of 1.8 mcg (n=6). Six patches were applied as a single dose to each swine for a total dose of 10.5 mcg. sMTS patches were prepared by attaching the array to an adhesive overlay with a diameter of 27 mm.

Animal testing was performed with young, nave, adult female mixed breed agricultural swine (Yorkshire X) with minimal skin pigmentation. The animals weighed approximately 22 to 30 kilograms at dosing. All animals were anesthetized prior to patch application. The test sites (ham) were prepared by clipping, shaving, and scrubbing with a 3M Buf Puf and soapy water. Finally the test sites were cleaned with a gauze pad soaked in 70% isopropyl alcohol solution and allowed to dry for at least 2 minutes prior to patch application. A single sMTS patch was applied to each of six test sites at time 0. The patches remained on the skin for 30 minutes before removal. The skin surface was swabbed after patch removal and residual rhGH left on the skin surface was determined by HPLC. Residual rhGH on the post-application patch was also determined by HPLC. The difference between the initial content and the residual left on the skin and patch was used to determine a net delivered dose of 10.0 mcg.

Figure 4:
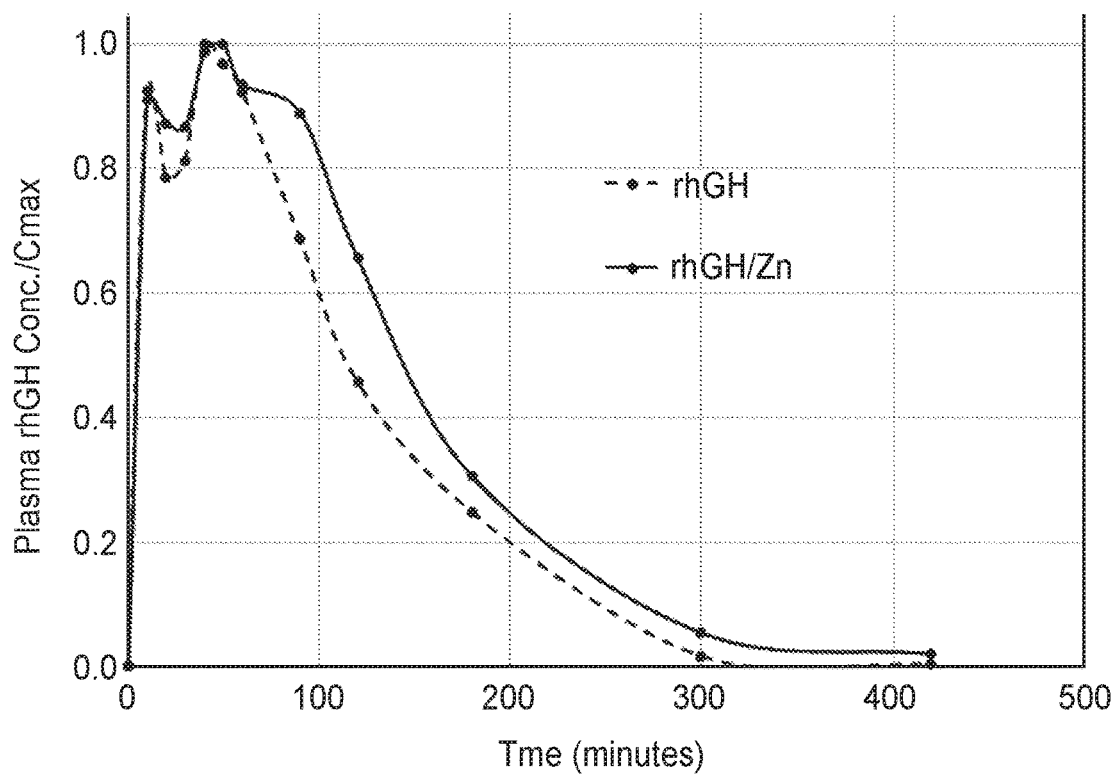
FIG. 4 is a graph of plasma rhGH concentration/Cmax vs. time.

Blood draws (1.5 mL per time point) were taken from an ear vein at times 0 min (pre-application), 10 min, 20 min, 30 min, 40 min, 50 min, 60 min, 90 min, 120 min, 180 min, 300 min, and 420 min. Plasma sample volume was approximately 0.7 mL. Plasma was stored at −70° C. prior to analysis. Plasma samples were assayed using ELISA assay kits. rhGH standards were run on each individual plate to determine a standard curve for that plate. The average plasma levels (n=4) normalized by Cmax are shown in FIG. 4 as a solid line.

Comparative Example 2—rhGH

A coating formulation was prepared consisting of 1.3% rhGH, (available from ProSpec-Tany TechnoGene Ltd., Ness Ziona, Israel), hydroxyethylcellulose 100 cP solution (2.3%), sucrose (40.0%), and water for injection (56.5%). sMTS patches were prepared as described in Example 2. The coated arrays were analyzed for rhGH content by HPLC and had an average content of 1.8 mcg (n=6). Six patches were applied as a single dose to each swine for a total dose of 11.0 mcg. The net delivered dose was 10.7 mcg. Animal testing and analysis was performed as described in Example 1. The average plasma levels (n=4) normalized by Cmax are shown in FIG. 4 as a dashed line.

Various embodiments of ZINC COMPOSITIONS FOR COATED MICRONEEDLE ARRAYS are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. A medical device comprising:
a composition comprising a therapeutically active amount of an active agent;
a zinc compound selected from the group consisting of zinc, pharmaceutically acceptable salts of zinc, and mixtures thereof; and
an array of microneedles,
wherein at least a portion of the composition is present as a coating on at least a portion of the microneedles; and
wherein the amount of zinc compound is 0.5% to 10% of the total weight of the composition.

2. A medical device according to claim 1, wherein the zinc compound comprises an inorganic salt of zinc.

3. A medical device according to claim 2, wherein the zinc compound comprises a divalent salt of zinc.

4. A medical device according to claim 3, wherein the zinc compound comprises zinc chloride or zinc acetate.

5. A medical device according to claim 1, wherein the molar ratio of zinc compound to active is 0.1 to 2.0.

6. A medical device according to claim 5, wherein the molar ratio of zinc compound to active is 0.2 to 1.5.

7. A medical device according to claim 6, wherein the molar ratio of zinc compound to active is 0.25 to 1.0.

8. A medical device according to claim 1, wherein the active agent is a protein or peptide.

9. A medical device according to claim 1, wherein the active agent is selected from the group consisting of human growth hormone (hGH), tissue plasminogen activator (TPA), calcitonin gene related peptide (CGRP), leutinizing hormone releasing hormone (LHRH), goserelin, leuprolide, buserelin, triptorelin, gonadorelin, napfarelin, menotropins, follicle stimulating hormone (FSH), leutinizing hormone (LH)), human menopausal goanadotropins (hMG), human chorionic gonadotropin (hCG), vasopressin, desmopressin, insulin, adrenocortiocotropic hormone (ACTH), ACTH (1-24), calcitonin, parathyroid hormone (PTH), parathyroid hormone antagonists, parathyroid hormone-related protein (PTHrP), oxytocin, deamino [Val4, D-Arg8] arginine vasopressin, interferon alpha, interferon beta, interferon gamma, tumor necrosis factor (TNF), erythropoietin (EPO), granulocyte macrophage colony stimulating factor (GM-CSF), granulocyte colony stimulating factor (G-CSF), interleukins, interleukin-2 (IL-2), interleukin-10 (IL-10), glucagon, and growth hormone releasing factor (GRF).

10. A medical device according to claim 1, wherein more than 50% by weight of the composition is present as a coating on the microneedles.

11. A medical device according to claim 10, wherein more than 75% by weight of the composition is present as a coating on the microneedles.

12. A medical device according to claim 11, wherein more than 90% by weight of the composition is present as a coating on the microneedles.

13. A method of delivering a therapeutically active agent to a mammal, comprising: applying a device according to claim 1 to a skin surface of the mammal, allowing the device to remain in contact with the skin for a period of time to allow a portion of the active agent to be transferred into the skin of the mammal, and subsequently removing the device from the mammal.

14. A method of delivering a therapeutically active agent to a mammal according to claim 13, wherein the Cmax attained in the mammal is greater than the Cmax that would be attained if a like device with a composition lacking zinc compound were applied to the mammal for the period of time.

15. A method of delivering a therapeutically active agent to a mammal according to claim 13, wherein the AUC attained in the mammal is greater than the AUC that would be attained if a like device with a composition lacking zinc compound were applied to the mammal for the period of time.

16. A medical device according to claim 1, wherein the active agent is not a PTHrP analogue.

17. A method according to claim 13, wherein the active agent is not a PTHrP analogue.

18. A medical device according to claim 1, wherein the amount of zinc compound is 1% to 8% of the total weight of the composition.

19. A medical device according to claim 18, wherein the amount of zinc compound is 2% to 6% of the total weight of the composition.

* * * * *

UNITED STATES PATENT AND TRADEMARK OFFICE
CERTIFICATE OF CORRECTION

PATENT NO. : 10,695,289 B2
APPLICATION NO. : 15/766469
DATED : June 30, 2020
INVENTOR(S) : Kenneth E. Brown et al.

It is certified that error appears in the above-identified patent and that said Letters Patent is hereby corrected as shown below:

In the Claims

In Column 18, Claim 18, Line 13, the '$^{8}$%' should read -- 8% --.

Signed and Sealed this
Second Day of May, 2023

Katherine Kelly Vidal
*Director of the United States Patent and Trademark Office*